(12) United States Patent
Coorey et al.

(10) Patent No.: US 9,051,237 B2
(45) Date of Patent: Jun. 9, 2015

(54) BIOGAS TO LIQUID FUEL CONVERTER

(76) Inventors: Peter Coorey, Lantau Island (HK); Wesley C. Broomham, Canowindra (AU)

(*) Notice: Subject to any disclaimer, the term of this patent is extended or adjusted under 35 U.S.C. 154(b) by 722 days.

(21) Appl. No.: 13/442,179

(22) Filed: Apr. 9, 2012

(65) Prior Publication Data

US 2013/0267614 A1 Oct. 10, 2013

(51) Int. Cl.
| C07C 27/00 | (2006.01) |
| C07C 29/151 | (2006.01) |
| C10L 3/08 | (2006.01) |
| C10K 1/02 | (2006.01) |
| C10K 1/04 | (2006.01) |
| C10K 3/02 | (2006.01) |
| C10L 3/10 | (2006.01) |

(52) U.S. Cl.
CPC ............. *C07C 29/1518* (2013.01); *C10L 3/10* (2013.01); *C10L 3/08* (2013.01); *C10K 1/024* (2013.01); *C10K 1/04* (2013.01); *C10K 3/026* (2013.01); *Y02E 50/346* (2013.01)

(58) Field of Classification Search
CPC ............. C10L 3/00; C10L 3/10; Y02E 60/50; C10G 3/00; B01J 19/2435; C07C 1/042; C07C 2/08
USPC ....... 48/197 R, 127.5, 127.7, 127.3; 422/625, 422/626, 629, 614, 616; 518/702, 705, 708
See application file for complete search history.

(56) References Cited

U.S. PATENT DOCUMENTS

| 5,500,449 | A * | 3/1996 | Benham et al. ............... 518/700 |
| 5,518,526 | A * | 5/1996 | Baksh et al. .................... 95/100 |
| 6,090,312 | A * | 7/2000 | Ziaka et al. ................... 252/373 |
| 6,601,543 | B2 * | 8/2003 | Rautenbach et al. ............. 123/3 |
| 6,802,974 | B2 * | 10/2004 | Rebholz et al. ............... 210/603 |
| 7,169,821 | B2 * | 1/2007 | Branson ....................... 518/702 |
| 8,809,603 | B2 * | 8/2014 | Corradini et al. ............... 585/14 |
| 2003/0111410 | A1 * | 6/2003 | Branson ....................... 210/603 |
| 2005/0266540 | A1 * | 12/2005 | Offerman et al. ............. 435/161 |
| 2007/0010588 | A1 * | 1/2007 | Pearson ....................... 518/701 |
| 2008/0032394 | A1 * | 2/2008 | Offerman et al. .......... 435/290.1 |
| 2008/0220489 | A1 * | 9/2008 | Offerman ...................... 435/157 |

OTHER PUBLICATIONS

Kralj, et al., "Methanol Production from Biogas", International Journal of Mathematics and Computers in Simulation, Issue 2, vol. 4, 2010, pp. 34-41.
Biofuel Fact Sheet, "Methanol from Biomass" 2 pp.

* cited by examiner

Primary Examiner — Nina Bhat
(74) Attorney, Agent, or Firm — Sheridan Law, LLC

(57) ABSTRACT

Described is a biogas to liquid fuel converter and method of use which includes a biogas cleaning system which can be obtained from a landfill of sewage digester which further includes a cargo container housing the syngas production system and methanol synthesis devices employed in converting biogas to methanol.

20 Claims, 3 Drawing Sheets

BIOGAS TO LIQUID FUEL CONVERTER

BACKGROUND

Generally, biogas to liquid fuel converters utilize very large scale processes requiring large amounts of equipment and large amounts of investment capital. These converters require very large amounts of bio-gas at a site to justify construction and operation of large scale methanol production. The Lurgi process for low-pressure crude methanol production from bio-gas is one example of a very large scale operation. Reduction of the size of an operation using the Lurgi process or other known processes is not possible by substituting smaller components for larger components. A new process, with components different than currently utilized components, is necessary to convert biogas into methanol.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a biogas to liquid fuel converter, comprising a gas cleaning system having a condensate separation vessel configured to remove moisture from a gas, and a polypropylene filter to remove particles; a syngas production system configured to receive the gas from the gas cleansing system, the syngas production system having a catalyst configured to produce hydrogen and carbon monoxide, and a flash tank to condense methanol from the gas; and a methanol synthesis system having a methanol synthesis reactor having catalysts configured to react with the gas at a temperature and a pressure to produce methanol.

In another embodiment, there is provided a biogas to liquid fuel converter, comprising a gas cleaning system; and a cargo container in fluid communication with the gas cleaning system, the cargo container comprising a syngas production system configured to receive the gas from the gas cleansing system, the syngas production system having a syngas reactor with a gas-to-gas re-heater, a heat exchanger, a syngas reactor, a catalyst configured to produce hydrogen and carbon monoxide, and a flash tank to condense methanol from the gas; and a methanol synthesis system having a methanol synthesis reactor having catalysts configured to react with the gas at a temperature and a pressure to produce methanol.

In yet another embodiment, there is provided a method of making a liquid fuel comprising converting one of a landfill gas and a sewage digester gas using a biogas to liquid fuel converter, comprising a gas cleaning system; and a cargo container in fluid communication with the gas cleaning system, the cargo container comprising a syngas production system configured to receive the gas from the gas cleansing system, the syngas production system having a syngas reactor with a gas-to-gas re-heater, a heat exchanger, a syngas reactor, a catalyst configured to produce hydrogen and carbon monoxide, and a flash tank to condense methanol from the gas; and a methanol synthesis system having a methanol synthesis reactor having catalysts configured to react with the gas at a temperature and a pressure to produce methanol.

Other objects, features, and advantages of the invention will become apparent from the following detailed description of the invention with reference to the accompanying drawings.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1A:
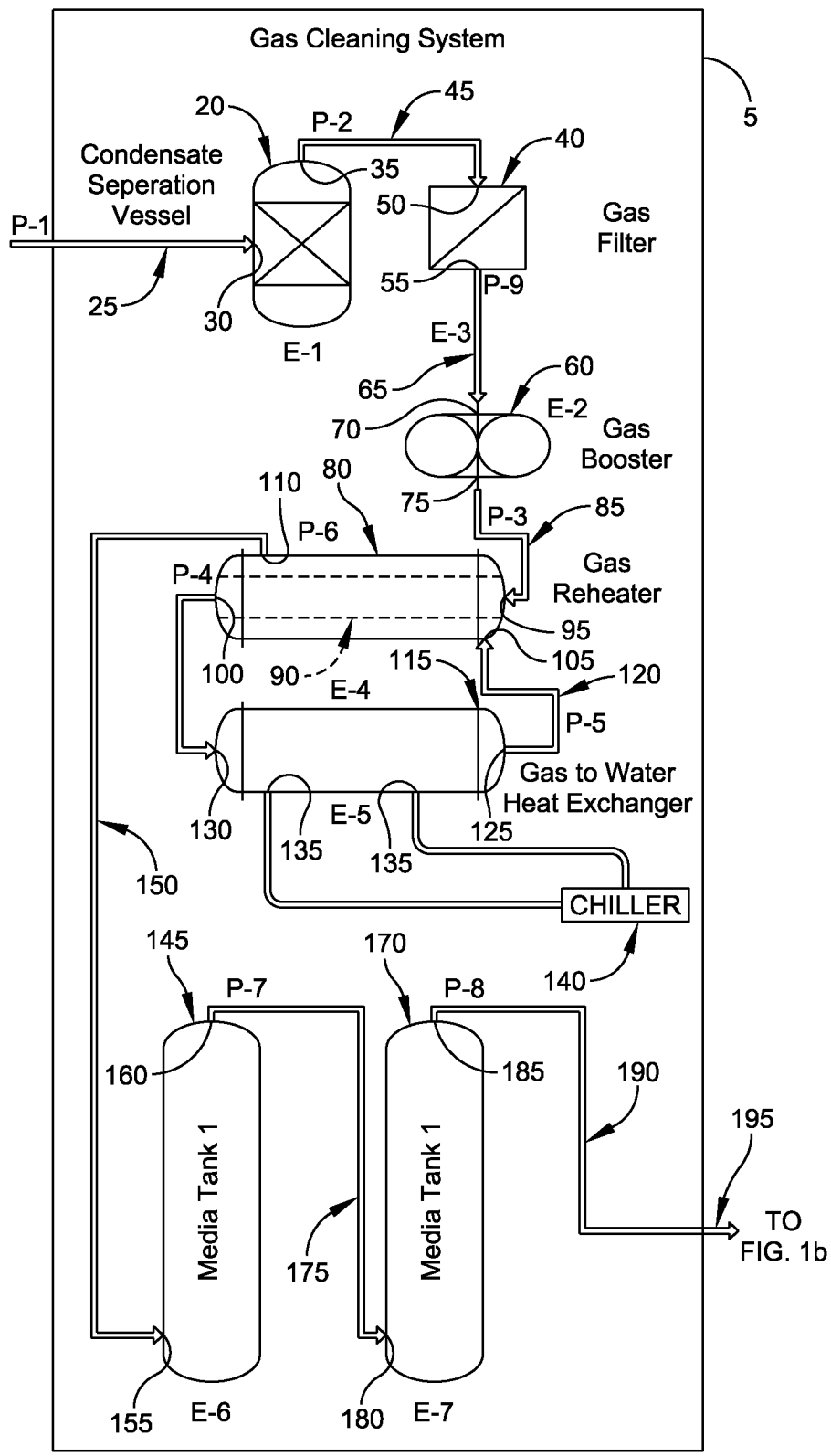
FIG. 1a illustrates a schematic representation of an exemplary embodiment of a gas cleaning system.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

This invention cleans, and converts bio-gas into liquid methanol at much lower temperature, pressure, with significantly lower water energy use than is current, and on a microscale that is many times smaller than any current technology allows.

The system is designed to be used with landfill gas or sewage digester gas, unique feed sources for conversion to liquid fuels, or other bio-gases (i.e. coal bed methane, low heating value natural gas). Other fuels that the system may produce include, but are not limited to: distillate having up to 75% diesel and no impurities; di-methyl ether for use in the chemical industry; methanol for use as a fuel or chemical intermediate; ethanol for use as a fuel or chemical intermediate; mixed alcohols-ethanol, methanol, butanol for higher octane fuels; chemical intermediates such as acrylates for polymer production; jet kerosene; and hydrogen.

It is a fraction of the size of any known gas to liquid plant; it is dramatically smaller than any comparable system because it is radically more efficient than any such system, requiring significantly less energy and water to be productive (and profitable). It is this ultra-reduction in scale that has made landfill and sewage gases viable—even the largest known landfills or sewage plants are not viable for fuel production (economies of scale). We are viable for app. 80% of all landfills in US.

The system may be installed in a shipping container for safety, noise reduction, and ease of transport. This may provide a form of mass production able to be transported where required because of the tiny scale.

In an embodiment, the system has 3 main components (1) a gas cleaning system, (2) a syngas production system, and (3) methanol synthesis system.

Fuel comes from the fuel supply, e.g. landfill, sewage plant digester, or bio gas from natural sources. We believe that our use of feed supplies such as landfill and sewage digester gas for the purpose of conversion to liquid fuels (technically alcohols) is unique.

The gas cleaning system is essential to the overall gas to liquid system. This cleaning system protects the syngas reaction from being poisoned, which would deactivate the catalyst within a few hours.

Gas Cleaning is achieved by first using a condensate separation vessel to remove larger particles of moisture, then a polypropylene filter to remove foreign particles down to 4 microns. After pre-cleaning the gas is the compressed to 7 Bar, after compression the gas is cooled down to 10 Degrees C. to remove the remainder of the moisture, then the gas is fed back through a re-heater and fed into the first media tank, where most of the siloxanes and other contaminants are removed, the gas exits out the top and is fed into the second media tank to remove any remaining siloxanes and contaminants. Tests are carried out to ensure the gas is within limits and siloxanes and $H_2S$ are not detectable (ND).

The gas is then fed into the syngas reactor. Syngas production is where the bio gas (60% CH4 40% CO2) is converted into a mixture of $H_2$ and CO. It is first preheated to 400 Degrees in a gas to gas re-heater, steam is then added, and then it enters the main heat exchanger and is heated to 900 degrees C. The heated gas is then fed into the syngas reactor and reacted over a catalyst to produce $H_2$ and CO. The gas is first cooled in the gas to gas re-heater, this cools the gas (and preheats the incoming gas), it is then fed into a gas to water heat exchanger and cooled to below 50 C, and moisture is removed with a cyclone filter. It is then fed into the gas compressor and compressed to 20 Bar, the gas is heated to 250 C. and fed into the methanol synthesis reactor, it leaves the reactor and is cooled to 25 degrees, it the is fed into a flash tank, a pressure drop of 15 bar is needed to condense the methanol from the gas, it is collected at the bottom of the tank and drained for final distillation. The left over gas mixture is fed back into the main manifold and used in the power plant.

For methanol synthesis, the syngas is then compressed to 20 bar and fed into the methanol synthesis reactor. The pressure is then dropped back to 5 bar and liquid methanol is separated. The conversion of landfill gas happens at just above atmospheric pressure, so no compressor that uses power in turn saves energy, and we re-use the heat from the first reaction to preheat the incoming gas, by using Steam CO2 reforming at low pressure is our main saving in energy, water can be recycled and used again. Catalysts are used that react at low pressure and temperature, which are included the second stage, 20 bar and 230 degrees, and which are much lower than conventional systems In an embodiment, there may be provided a gas cleaning system 5 (see FIG. 1*a*); a syngas production system 10 (see FIG. 1*b*); and a methanol synthesis system 15 (see FIG. 1*c*).

With reference to FIG. 1*a*, and in an embodiment, there may be provided a gas cleaning system 5 external to the remainder of the gas-to-liquid system (referred to as a "GTL system") inside a shipping container or other modular container. In an embodiment, cleaning system 5 is separate due to size and may be skid mounted with a couple of large media tanks. Generally, the only part of the gas-to-liquid system that needs to be replaced is the catalysts, which have a 3 to 5 year life expectancy. Gas cleaning system 5 uses a media that can be regenerated every 3 months.

Still looking at FIG. 1*a*, there may be provided a condensate separation vessel 20 to receive methane gas from a transport pipe 25 into a side entry inlet 30. Condensate separation vessel 20 may be provided as a vertical tank sized 4000 mm by 1500 mm. Condensate separation vessel 20 may be made from stainless steel. Side entry inlet 30 may be flanged and have a width of 300 mm. Side entry inlet 30 may be located about 2000 mm from bottom of the tank forming condensate separation vessel 20. A side exit 35 may be provided from condensate separation vessel 10. Side exit 35 may be located about 500 mm from top of the tank forming condensate separation vessel 20. Side exit 35 may be flanged and have a width of 300 mm.

A gas filter 40 may be provided in fluid connection to side exit 35 of the condensate separation vessel 10. A transport pipe 45 may be disposed between gas filter 40 and condensate separation vessel 20. Gas filter 40 may include a stainless steel filter box having dimensions of a length of 500 mm by a width of 1000 mm by a height of 750 mm. The stainless filter box of the gas filter 40 may include a 4-micron polypropylene filter. In an embodiment, a gas inlet 50 of gas filter 40 has a width of 300 mm and a gas outlet 55 of gas filter 40 has a width of 200 mm.

A gas booster 60 may be provided in fluid connection to gas filter 40. Gas booster 60 may include a gas compressor, e.g., a 90SCMH Hitachi gas compressor. A transport pipe 65 may be disposed between gas booster 60 and gas filter 40. In an embodiment, a gas inlet 70 of gas booster 60 has a width of 200 mm and a gas outlet 75 of gas booster 60 has a width of 50 mm.

A gas reheater 80 may be provided in fluid connection to gas booster 60. A transport pipe 85 may be disposed between gas reheater 80 and gas booster 60. Gas reheater 80 may be formed include a tank sized 450 mm by 1500 mm. In an embodiment, gas reheater 80 includes a stainless steel shell and tube heat exchanger 95 formed of SS 304L (an austenitic Chromium-Nickel stainless steel offering the optimum combination of corrosion resistance, strength, and ductility.) In an embodiment, an inner tube gas inlet 90 of gas reheater 80 is flanged and has a width of 50 mm and an inner tube gas outlet 100 of gas reheater 80 is flanged and has a width of 50 mm. An outer tube (i.e., shell) gas inlet 105 of gas reheater 80 is flanged and has a width of 50 mm and an outer tube (i.e., shell) gas outlet 110 of gas reheater 80 is flanged and has a width of 50.

A gas to water heat exchanger 115 may be provided as a tank sized 450 mm by 1500 mm. Gas to water heat exchanger 115 may be made from 304 stainless steel as a tube heat exchanger. A transport pipe 120 may be disposed in fluid connection between gas reheater 80 and gas to water heat exchanger 115. A side entry inlet 125 may be provided into gas to water heat exchanger 115. Side entry inlet 125 may be flanged and have a width of 50 mm. A side outlet 130 may be provided from gas to water heat exchanger 115. Side outlet 130 may be flanged and have a width of 300 mm. Water connections 135 may be provided between gas to water heat exchanger 115 and a chiller 140 to circulate water or other fluid to cool the methane gas provided through gas to water heat exchanger 115. In an embodiment, this circulated water may be configured to flow at a rate of about 90 liters per minute. Chiller 140 may include, but is not limited to, a Trane brand 90 liter per minute chiller device. In an embodiment, chiller 140 may operate at about 10 degrees C. to provide cooled water to the tube heat exchanger 115. A media tank 145 (also referred to as media tank 1) may be provided as a 304 stainless steel tank sized 650 mm by 3000 mm. A transport pipe 150 may be disposed in fluid connection between gas to water heat exchanger 115 and media tank 145. An inlet connection 155 may be provided into media tank 145. Inlet connection 155 may be flanged and may have a width of 50 mm. An outlet connection 160 may be provided from media tank 145. Outlet connection 160 may be flanged and have a width of 50 mm. Media tank 145 contains an area of carbon granules of about 2.5 mm by 5 mm. Media tank 145 must include about 1 gram of activated carbon covering a surface area in excess of 500 $m^2$.

A media tank 170 (also referred to as media tank 2) may be provided as a 304 stainless steel tank sized 650 mm by 3000 mm. A transport pipe 175 may be disposed in fluid connection between media tank 145 and media tank 170. An inlet connection 180 may be provided into media tank 145. Inlet connection 180 may be flanged and may have a width of 50 mm. An outlet connection 185 may be provided from media tank 170. Outlet connection 185 may be flanged and have a width of 50 mm. Media tank 170 contains an area of carbon granules of about 2.5 mm by 5 mm. Media tank 170 must include about 1 gram of activated carbon covering a surface area in excess of 500 m$^2$. A line 190 may be in fluid connection with outlet connection 185 to output 195 of gas cleaning system 5.

Figure 1B:
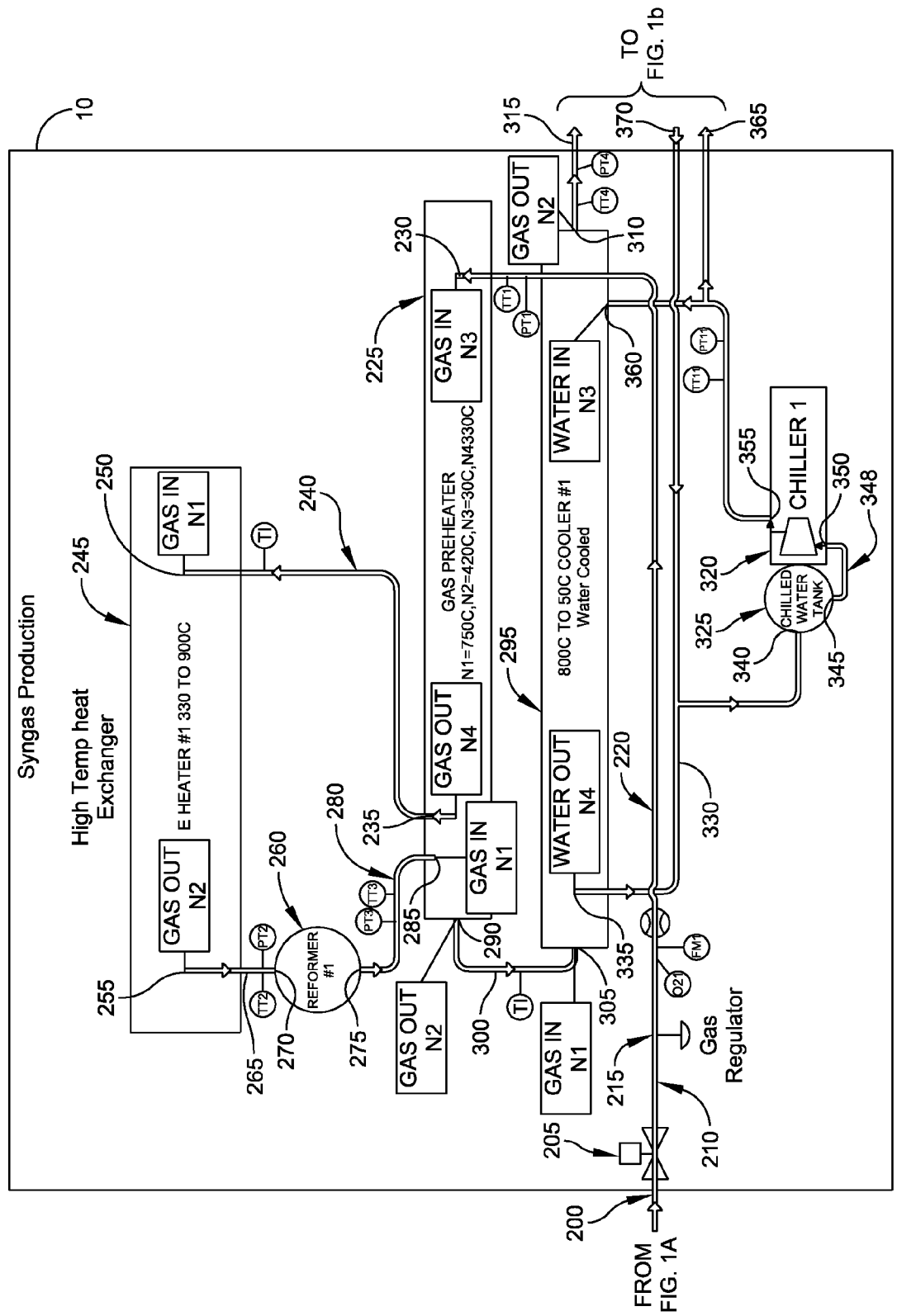
FIG. 1b illustrates a schematic representation of an exemplary embodiment of a syngas production system.

With reference to FIG. 1b, and in an embodiment, there may be provided syngas production system 10 within a shipping container or other modular container. Syngas production system 10 may include piping all formed from 50 mm schedule 80 304L stainless steel. An input line 200 may be in fluid connection with line 190 from gas cleaning system at output 195. A gas isolation valve 205 may be provided prior to a line 210 to a gas regulator 215. Gas isolation valve 205 may be a 50 mm pneumatically controlled valve. Gas regulator 215 may reduce the pressure of the cleaned methane gas from 7 Bar to 1 Bar into a line 220. Gas regulator 215 may include a 50 mm flanged connection with line 210 and line 220.

A gas reheater 225 may be provided in fluid connection with line 220 at inlet 230 with a 50 mm flanged connection and include an outlet 235 with a 50 mm flanged connection to line 240. Gas reheater 225 may be formed of a tank of stainless steel 304 forming a shell and tube heat exchanger having dimensions with a diameter of 300 mm by a length of 2400 mm.

An electric heat exchanger 245 may be provided in fluid connection with gas reheater 225 through line 240 to an inlet 250 having a 50 mm flanged connection. An outlet 255 may be provided with a 50 mm flanged connection. Electric heat exchanger may operate over a range of 0 to 900 Degrees C. Electric heat exchanger 245 may be formed of 304L stainless steel and have dimensions with a diameter of 300 mm by a length of 2400 mm.

A reactor 260 (also referred to as a reformer 1) may be provided in fluid connection to electric heat exchanger 245 with a line 265. An inlet 270 with a flanged connection with a width of 100 mm may be provided between reactor 260 and line 265. An outlet 275 with a flanged connection with a width of 100 mm may be provided from reactor 260. Reactor may include a stainless steel 304L tube in a U configuration, which is generally shown as a pressure vessel. A transport pipe or line 280 may extend from outlet 275 to a gas inlet 285 at gas reheater 225.

An outlet 290 may be in fluid communication from a water-cooled heat exchanger 295 to gas reheater 225 with a transport pipe or line 300. Water-cooled heat exchanger 295 may include a 50 mm flanged connection 305 to line 300. Water-cooled heat exchanger 295 may include a pipe having a width of 100 mm. Water flow through the water-cooled heat exchanger 295 may proceed at a rate of 90 liters per minute. Water-cooled heat exchanger 295 may have dimensions of a diameter of 300 mm by a length of 2400 mm and may be formed of stainless steel 304L. Water-cooled heat exchanger 295 cools the gas from about 800 degrees C. to about 50 degrees C. from inlet 305 to gas outlet 310. A transport pipe or line 315 leads from gas outlet 310 to methanol synthesis system 15.

A chiller 320 in fluid connection with water-cooled heat exchanger 295 may include a chilled water tank 325 receiving water out through a transport pipe or line 330 from an outlet 335 in connection with water-cooled heat exchanger 295. In an embodiment, chiller 320 may include a Trane brand 90 liter per minute chiller device. An inlet 340 may connect line 330 to chilled water tank 325. An outlet 345 may connect a line 348 to chilled water tank 325. An inlet 350 may connect line 348 to chiller 320. An outlet 355 may connect chiller 320 to an inlet 360 of water-cooled heat exchanger 295 and to a transport pipe or line 365 to methanol synthesis system 15.

Figure 1C:
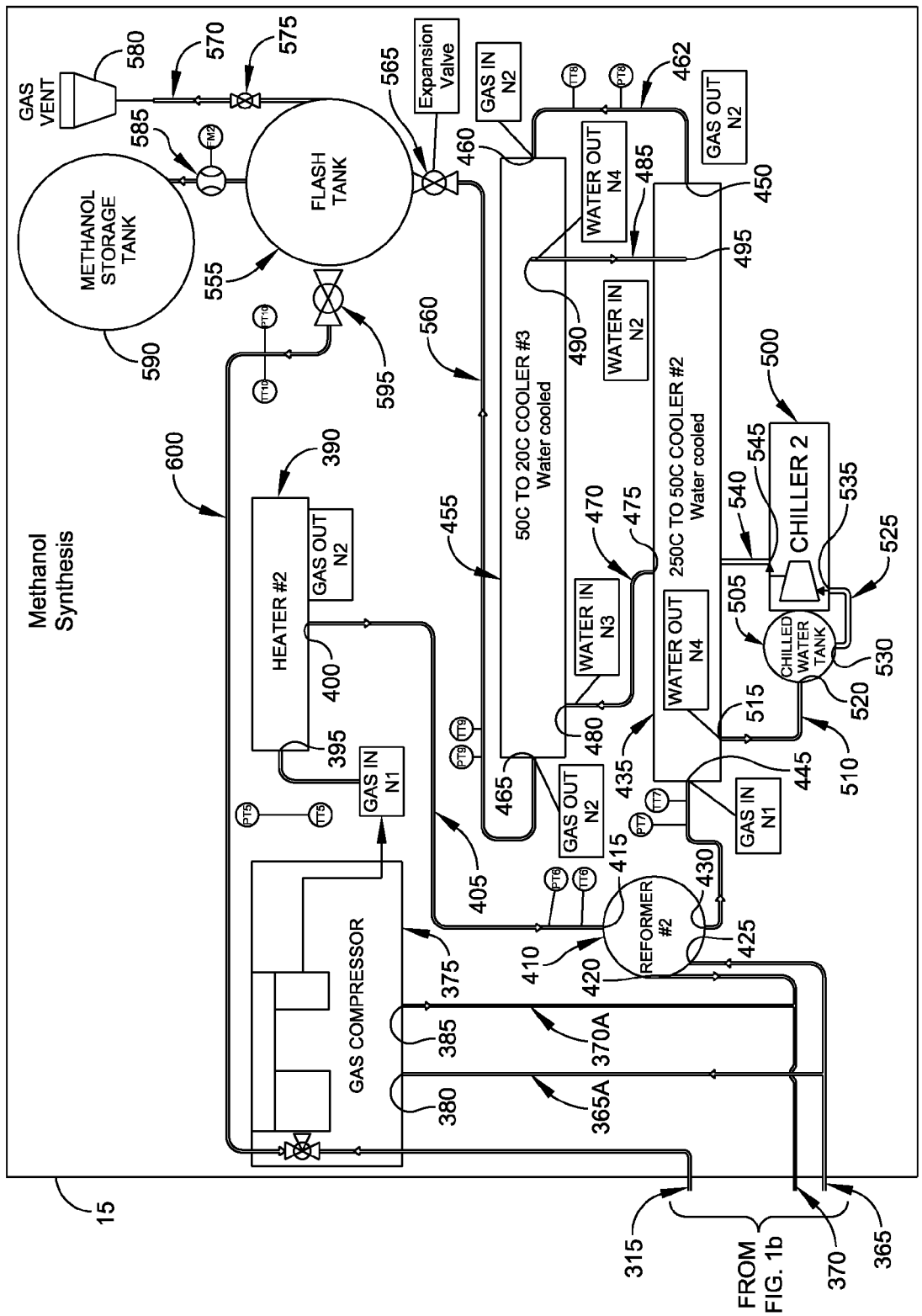
FIG. 1c illustrates a schematic representation of an exemplary embodiment of a methanol synthesis system.

With reference to FIG. 1c, and in an embodiment, methanol synthesis system 15 may include all pipe work of stainless steel 304L having a diameter of 50 mm.

A gas compressor 375 may be provided in fluid connection with a line 315 from syngas production system 10. Gas compressor 375 may include a Corken brand gas compressor operating at 60 standard cubic meters per hour (SCMH), operating at a pressure of 25 Bar, and being water cooled. An inlet 380 of gas compressor 375 allows receipt of water from line 365A, which is connected with fluid line 365 from syngas production system 10. An outlet 385 of gas compressor 375 allows return of water through line 370A, which is connected to fluid line 370 returning to syngas production system 10.

An electrical heat exchanger 390 may have an inlet 395 to receive gas and an outlet to direct heated gas into a transport pipe or a line 405. The heated gas may have a temperature of about 150 degrees C. to 250 degrees C.

A synthesis reactor 410 (also referred to as a reformer 2) may include an inlet 415 in fluid communication with line 405 to receive the heated gas. Another inlet 425 may be in fluid communication with line 365 of syngas production 10 to receive chilled water into synthesis reactor 410 from chiller 355. An outlet 430 may be in fluid communication with synthesis reactor 410 to provide gas into a pressure shell and tube heat exchanger 435 from transport pipe or line 440 through inlet 445. Synthesis reactor 410 may be dimensioned at a size of 400 mm by 1600 mm. (This size ratio is proven technology.)

Pressure shell and tube heat exchanger 435 may be constructed of stainless steel 304L material and operate at a pressure of 30 Bar. An inlet 445 for gas into pressure shell and tube heat exchanger 435 may include a 50 mm flanged connection. Inlet 455 may be in fluid connection with line 440 from synthesis reactor 410. An outlet 450 for gas out of pressure shell and tube heat exchanger 435 may include a 50 mm flanged connection.

A pressure shell and tube heat exchanger 455 may be constructed of stainless steel 304L material and operate at a pressure of 30 Bar. An inlet 460 for gas into pressure shell and tube heat exchanger 455 may include a 50 mm flanged connection. A transport pipe or line 462 may be in fluid connection between outlet 450 of pressure shell and tube heat exchanger 435 and pressure shell and tube heat exchanger 455. An outlet 465 for gas out of pressure shell and tube heat exchanger 455 may include a 50 mm flanged connection.

For circulating cooling water between pressure shell and tube heat exchanger 435 and pressure shell and tube heat exchanger 455, a transport pipe or line 470 may be provided in fluid communication between these exchangers through water outlet 475 into pressure shell and tube heat exchanger 435 from water inlet 480 from pressure shell and tube heat exchanger 455. Another transport pipe or line 485 may be provided in fluid communication between these exchangers through water inlet 490 from pressure shell and tube heat exchanger 455 into water outlet 495 and into pressure shell and tube heat exchanger 435. Pressure shell and tube heat exchanger 435 may cool water from 250 degrees C. to 50 degrees C. Pressure shell and tube heat exchanger 455 may cool water from 50 degrees C. to 20 degrees C.

A second chiller 500 (also referred to as a chiller 2) may be configured with a chilled water tank 505 to receive water through a transport pipe or line 510 from an outlet 515 in pressure shell and tube heat exchanger 435. An inlet 520 in fluid connection with line 510 provides water to chilled water tank 505. A second transport pipe or line 525 may provide a fluid connection between an outlet 530 of chilled water tank 505 to an inlet 535 of chiller 500. A third transport pipe or line 540 may provide a fluid connection between an outlet 545 of chiller 500 and an inlet of pressure shell and tube heat exchanger 435. Chiller 500 may include a Trane brand 90 liter per minute chiller.

A flash tank 555 may be formed from stainless steel 304L. An input line 560 may extend in fluid communication from gas outlet 465 to flash tank 555. An expansion valve 565 may be configured between input line 560 and flash tank 555 to provide a drop in pressure of the water from 25 Bar to 5 Bar pressure.

A gas vent line 570 extends between flash tank 555 and includes a valve 575 prior to gas vent 580. In one embodiment, expansion valve 565 drops the pressure very quickly into a larger vessel, and, in turn, the gas vapors condense and form droplets of liquid. Vent 580 is for either venting to atmosphere or returning to the main header.

A storage tank line 585 extends between flash tank 555 and a methanol storage tank 590. In an embodiment, methanol liquid fuel may be removed from methanol synthesis system 15 from the methanol storage tank.

A valve 595 may be disposed within a water line 600 extending away from flash tank 555. Water line returns excess water from flash tank 555 to a water-cooled heat exchanger 295 of syngas production system 10 through line 315.

In reactor 260, reactor 410, or both, catalysts have included an experimental Nano catalyst that worked very well but was prone to coking and deactivation so it was decided to use a commercially available CAT. Both the CAT surgery are commercially available with unsized nanoscale particles.

Reactor 260 (also referred to as reformer 1) utilized the ReforMax® 330 brand product catalyst supplied from Sudchem. Reactor 410 (also referred to as reformer 2) utilized the UNI CAT-MS-900 brand product catalyst, which is the next generation UNICAT CuO/ZnO Low Temperature Active Methanol Synthesis catalyst. Other catalysts may also work to convert methane gas to liquid methanol fuel.

The combination of gas cleaning system 5, syngas production system 10, and methanol synthesis system 15 are operable at low temperature and pressure so as to reduce both manufacturing cost and operational cost for producing liquid methanol.

A number of operating parameters must be met for each of gas cleaning system 5, syngas production system 10, and methanol synthesis system 15 to work so as to produce liquid methanol. The main operating parameters that must be met are temperatures and pressures. These main parameters are provided by the syngas production system 10 and methanol synthesis system 15 to work so as to produce liquid methanol. Gas cleaning system 5 provides the necessary methane gas, which must be extremely clean.

Catalysts only operate at specific temperatures and pressures which are provided by the syngas production system 10 and methanol synthesis system 15

For high temperature operation and durability, the various parts described hereinabove may be fabricated from stainless steel 304L or higher equivalent properties for high temperature operation.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A biogas to liquid fuel converter, comprising:
a gas cleaning system having a condensate separation vessel configured to remove moisture from a gas, and a polypropylene filter to remove particles;
a syngas production system configured to receive the gas from the gas cleansing system, the syngas production system having a catalyst configured to produce hydrogen and carbon monoxide, and a flash tank to condense methanol from the gas; and
a methanol synthesis system having a methanol synthesis reactor having catalysts configured to react with the gas at a temperature and a pressure to produce methanol.

2. A biogas to liquid fuel converter in accordance with claim 1, wherein the gas cleaning system wherein the gas is one of a landfill gas and a sewage digester gas.

3. A biogas to liquid fuel converter in accordance with claim 1, wherein the polypropylene filter is configured to remove particles greater than 4 microns from the gas.

4. A biogas to liquid fuel converter in accordance with claim 1, further comprising a first media tank configured to remove contamination from the gas.

5. A biogas to liquid fuel converter in accordance with claim 4, further comprising a second media tank to remove remaining contaminants from the gas.

6. A biogas to liquid fuel converter in accordance with claim 1, wherein the syngas production system includes a syngas reactor with a gas-to-gas re-heater.

7. A biogas to liquid fuel converter in accordance with claim 1, wherein the syngas production system includes a heat exchanger.

8. A biogas to liquid fuel converter in accordance with claim 1, wherein the syngas production system includes a syngas reactor.

9. A biogas to liquid fuel converter in accordance with claim 1, wherein the pressure of the methanol synthesis reactor is about 20 bar and the temperature is about 230 degrees C.

10. A biogas to liquid fuel converter in accordance with claim 1, wherein the syngas production system and the methanol synthesis system are disposed together in a cargo container in fluid communication with the gas cleaning system.

11. A biogas to liquid fuel converter, comprising:
a gas cleaning system; and
a cargo container in fluid communication with the gas cleaning system, the cargo container comprising:
a syngas production system configured to receive the gas from the gas cleansing system, the syngas production system having a syngas reactor with a gas-to-gas re-heater, a heat exchanger, a syngas reactor, a catalyst configured to produce hydrogen and carbon monoxide, and a flash tank to condense methanol from the gas; and
a methanol synthesis system having a methanol synthesis reactor having catalysts configured to react with the gas at a temperature and a pressure to produce methanol.

12. A biogas to liquid fuel converter in accordance with claim 11, wherein the gas cleaning system wherein the gas is one of a landfill gas and a sewage digester gas.

13. A biogas to liquid fuel converter in accordance with claim 11, wherein the polypropylene filter is configured to remove particles greater than 4 microns from the gas.

14. A biogas to liquid fuel converter in accordance with claim 1, further comprising a first media tank configured to remove contamination from the gas.

15. A biogas to liquid fuel converter in accordance with claim 14, further comprising a second media tank to remove remaining contaminants from the gas.

16. A biogas to liquid fuel converter in accordance with claim 11, wherein the syngas production system includes a syngas reactor with a gas-to-gas re-heater.

17. A biogas to liquid fuel converter in accordance with claim 11, wherein the syngas production system includes a heat exchanger.

18. A biogas to liquid fuel converter in accordance with claim 11, wherein the syngas production system includes a syngas reactor.

19. A biogas to liquid fuel converter in accordance with claim 11, wherein the pressure of the methanol synthesis reactor is about 20 bar and the temperature is about 230 degrees C.

20. A method of making a liquid fuel comprising converting one of a landfill gas and a sewage digester gas using the converter of claim 11.

* * * * *